United States Patent [19]

McRae

[11] Plant 5,008

[45] Mar. 22, 1983

[54] LILY PLANT (LILIUM GOLDRUSH)

[75] Inventor: Edward A. McRae, Boring, Oreg.

[73] Assignee: Melridge, Inc., Sandy, Oreg.

[21] Appl. No.: 258,744

[22] Filed: Apr. 29, 1981

[30] Foreign Application Priority Data

Mar. 19, 1980 [NL] Netherlands ..... LEL 97

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant bearing large clusters of large flowers of excellent form, unusual color, and long persistence both on the plant and as cut flowers. The plant is characterized by rapid natural propagation under field conditions and vigorous and healthy growth when forced under glass. It is further characterized by early attainment of marketable bulb size and bulb maturity, relatively short foliage, foliage resistance to scorching, buds of a clear medium yellow color, and virtually unspotted flowers of a bright deep yellow color having tepals of increased breadth and thickness.

1 Drawing Figure

BACKGROUND AND GENERAL STATEMENT OF THE INVENTION

My new variety of lily is classified botanically as a Lilium hybrid; commercially, as an upright Asiatic hybrid, Division I-A in the Horticultural Classification of the Genus Lilium adopted by The Royal Horticultural Society of London.

My new variety of lily plant originated as a seedling selected from a group of seedlings among the seedling beds of test crosses of Oregon Bulb Farms at Sandy, Oreg. The cross was made in 1968 and the lily plant first flowered in 1970.

The cross was made during a breeding program having as its objective the production of brilliantly-colored, upright-flowering lily cultivars which would perform well when forced into flower under glass throughout the year, in addition to meeting the requirements of vigor, disease resistance, and rapid natural propagation and field growth. Cultivars were sought which would be disease resistant, virus tolerant, and not susceptible to leaf scorch or bud abortion when forced.

The cross was made between the seed parent Lilium 'Joan Evans' (unpatented) and the pollen parent: Lilium 'Connecticut King' (unpatented).

My new lily plant is characterized by rapid natural propagation under field conditions and vigorous and healthy growth when forced under glass. It is characterized further by early attainment of marketable bulb size and bulb maturity. The plant has relatively short foliage as well as foliage resistant to scorching when forced into flower under glass during winter.

The buds are of a clear, medium yellow color. The flowers are virtually unspotted and are distinctive in that they are a bright, deep yellow color having tepals of increased breadth and thickness.

Lilium 'Goldrush' most closely resembles the older cultivar 'Connecticut King', but has broader tepals and greater tepal thickness. Of primary interest, it attains marketable bulb size and bulb maturity more rapidly in the fall than does 'Connecticut King'. Its foliage is shorter and less liable to scorch when forced into flower under glass during the winter.

The buds are of a clear, medium yellow color. The flowers are of a bright, deep yellow color, virtually unspotted.

My new variety of lily plant has been asexually produced by me and under my direction at Oregon Bulb Farms, Sandy, Oreg. Successive generations produced by bulb scale propagation and natural propagation from below ground stem bulblets have demonstrated that the novel and distinctive characteristics of my new variety are fixed and hold true under asexual propagation from generation to generation.

THE DRAWING

My new variety of lily plant is illustrated in the accompanying photographs which show the plant, its foliage, and its buds in their various stages of development and in open bloom in full color.

DESCRIPTION OF THE NEW VARIETY

The following is a detailed description of my new variety of Asiatic hybrid lily with nomenclature according to the International Lily Register, The Royal Horticultural Society, London, Second Edition (1969) and with color designations according to The Royal Horticultural Society Color Chart, published by The Royal Horticultural Society in 1966.

THE PLANT

Form: Bulbous monocotyledon.

Height: Bulbs 12–15 cm in circumference, when forced under glass, average 50–60 cm (21–26″) tall; in the field, bulbs in their second season after scaling average 60–100 cm (24–38″) tall.

Growth: Vigorous, with considerable strength.

Foliage:

*Quantity.*—Abundant, about 80–100 leaves per stem.

*Size of leaves.*—About 6–8 cm (2–3″) long and 1.5 cm (¾″) wide.

*Shape of leaves.*—Lanceolate.

Texture of leaves: Leaves entire (not serrated), margins and axils glabrous (not pubescent).

*Color of leaves, upperside.*—Medium glossy green.

*Color of leaves, underside.*—Medium glossy green.

*Ribs and veins of leaves.*—Typical monocotyledonous venation; light green parallel veins.

INFLORESCENCE

Excellent compact raceme, with short pedicels and no secondary buds. Bulbs 12–15 cm in circumference produce an average of 6 to 8 buds.

Peduncle and pedicels are glabrous.

Strength of inflorescence: Strong and wirey.

Color of inflorescence: Medium glossy green with clear yellow buds.

THE BUDS

Size: 7–8 cm (3–3¾") long, 2–4 cm (¾–1¼") wide.

Form: Lanceolate with obtuse tip; typical of Asiatic hybrid lilies.

Opens slowly: Opens in about one hour in response to morning light; flowers further up the stem open on subsequent days over an interval of one to two weeks. Typical of Asiatic hybrid lilies.

Color of mature bud: Clear medium yellow (R.H.S. CC #12 B-C).

THE FLOWER

Blooms: Late June or early July in western Oregon, in midseason, once, profusely.

Size:

*Flower diameter.*—14–17 cm (5½–7").

*Inner tepals.*—4.0–4.5 cm (1½–1¾") wide.

*Outer tepals.*—2.5–3.0 cm (¾–1") wide.

Shape when bloom first opens: Shallow bowl-shape with recurving tips. Tepals recurve more as flower ages.

Tepal arrangement: Typical of the genus Lilium, with 6 entire, imbricated tepals.

*Color, outer tepal.*—Bright deep yellow (Royal Horticultural Society's Color Code #12A). (A 2 cm gold blush (R.H.S. CC#21A) covers base of outer tepals.)

*Color, inner tepal.*—Bright deep yellow (R.H.S. CC #12A). (A 2 cm-wide flush of gold (R.H.S. CC #21A) marks base of inner tepals).

*Color, reverse of tepals.*—Bright deep to medium yellow. (R.H.S. CC #12A-B).

The lower, detailed illustrated blossom is less yellow than the actual color because of the lighting conditions when photographed. The actual yellow color is better depicted in the upper illustrated blossom and is quite similar to the variety, Connecticut King.

Tepals remain on individual flowers 5–7 days; stem has flowers with tepals adhering for about 3 weeks.

Flower texture: Shiny, velvety. Not affected by hot or wet weather, although intensity of color may be reduced by extremely low light levels.

Tepals fall as flower ages.

Pedicel:

*Length.*—5–12 cm (2–4").

*Color.*—Medium to dark green. Sturdy and wirey, glabrous.

Disease resistance: To Botrytis blight and to Fusarium bulb rot.

Fragrance: None.

Lasting Quality: Flowers remain on plants for about three to four weeks. Flowers remain on cut-flower stems for about three weeks, with adequate light.

THE REPRODUCTIVE ORGANS

Stamens and anthers: Typical of genus Lilium. Six versatile anthers hang (singly) from six filaments.

Filaments: 5–6 cm (2") long and light yellow.

Pollen: Deep gold to golden brown.

Pistil: 1, typical of genus Lilium. Style is 5–6 cm (2") long.

Stigma: Small, three-lobed, soft yellow with very light plum overlay, velvety texture.

Ovary: Typical of genus Lilium. Superior, single, 6-chambered ovary.

THE FRUIT

Fertile, an ovoid to oblong capsule with 6 chambers.

Color at maturity: Medium green sometimes overlaid with pale magenta-plum. Fades to soft brown when fruit splits open to release seeds.

THE BULBS

Color of bulbs: White.

Size of bulbs: Usual commercial size is 12–20 cm (5–8") in circumference; bulbs can reach much larger size if desired.

I claim:

1. A new and distinctive variety of Asiatic hybrid lily plant substantially as herein shown and described, characterized by its rapid natural propagation under field conditions, vigorous and healthy growth when forced under glass, and uniform growth to maturity when forced to flower throughout the year; by its early attainment of marketable bulb size and bulb maturity; relatively short foliage; foliage resistant to scorching when forced into flower under glass during the winter; buds of a clear, medium yellow color; and virtually unspotted flowers of bright, deep yellow color having tepals of increased breadth and width.

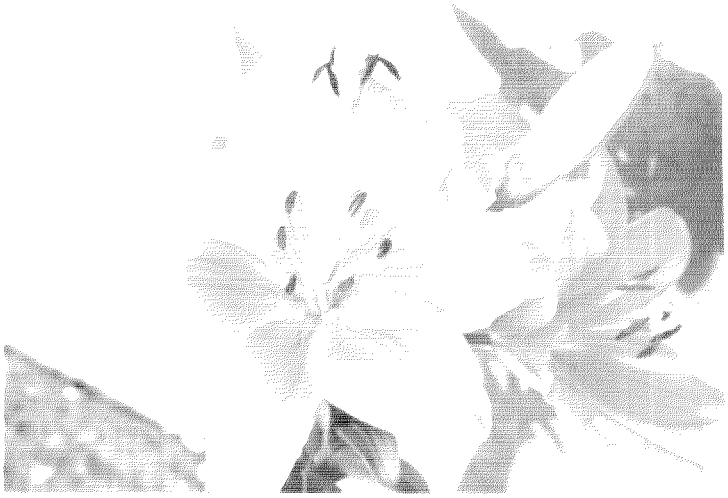
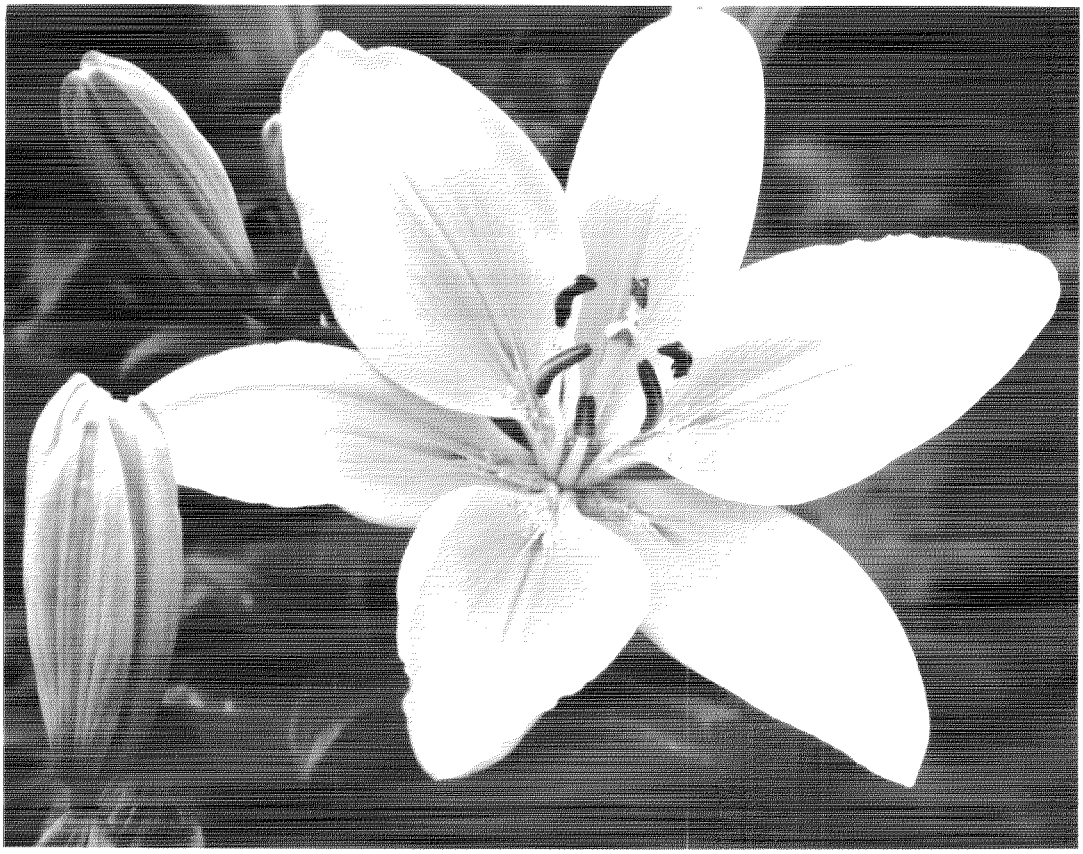

* * * * *